United States Patent [19]
Wilder et al.

[11] Patent Number: 4,606,735
[45] Date of Patent: Aug. 19, 1986

[54] MEDICAL TUBING HOLDER

[76] Inventors: Joseph R. Wilder, 151 W. 86th St., Apt. 9D, New York, N.Y. 10024; Franklin G. Reick, 228 W. Place, Westwood, N.J. 07675

[21] Appl. No.: 653,718

[22] Filed: Sep. 24, 1984

[51] Int. Cl.$^4$ .............................. A61M 25/02
[52] U.S. Cl. .................... 604/180; 248/74.2; 248/205.3; 128/DIG. 26
[58] Field of Search ............ 604/180, 179, 174; 128/DIG. 26, 133, DIG. 15; 248/205.2, 205.3, 74.1, 74.2

[56] References Cited

U.S. PATENT DOCUMENTS

| | | | |
|---|---|---|---|
| 3,210,816 | 10/1965 | Clemons | 128/DIG. 26 |
| 3,286,713 | 11/1966 | Kurtz | 128/DIG. 26 |
| 3,288,137 | 11/1966 | Lund | 604/180 |
| 3,368,564 | 2/1968 | Selix | 604/180 |
| 3,630,195 | 12/1971 | Santomieri | 604/180 |
| 3,702,612 | 11/1972 | Schlesinger | 248/205.3 |
| 3,812,851 | 5/1974 | Rodriguez | 604/179 |
| 3,826,254 | 6/1974 | Mellor | 604/180 |
| 4,239,046 | 12/1980 | Ong | 128/DIG. 15 |

FOREIGN PATENT DOCUMENTS 1199543 1/1965 Fed. Rep. of Germany ..... 248/74.1

Primary Examiner—Dalton L. Truluck
Assistant Examiner—Karen L. Kaechele
Attorney, Agent, or Firm—Michael Ebert

[57] ABSTRACT

A detachable holder for immobilizing a flexible tubing at a site adjacent its point of connection to a medical device inserted in a patient to feed a therapeutic fluid into a vein or artery or to withdraw fluid from the patient. The holder is formed by a flexible plastic strip having upstanding end wings provided with snap-in key hole slots in axial alignment. These slots are adapted to receive a short section of the tubing which then bridges the wings and is held thereby. Attached to the underside of the strip is one component of a hook and loop fabric fastener whose other component is bonded to the outer face of an adhesive tape. By adhering the tape to the skin of the patient at a position adjacent the inserted medical device and then fastening the holder thereto, one is able to immobilize the tubing to prevent a tug thereon from displacing the inserted medical device.

5 Claims, 5 Drawing Figures

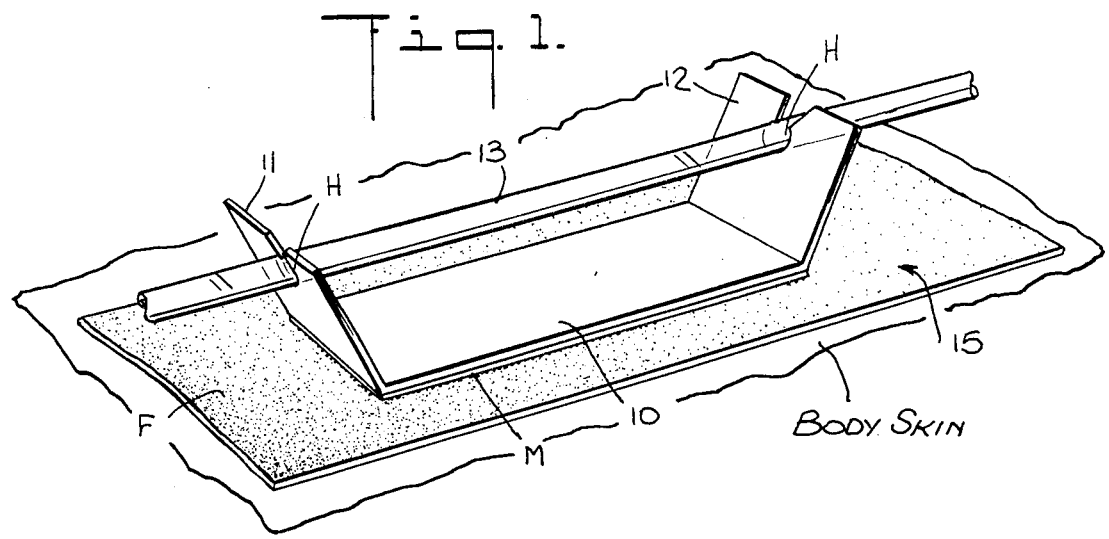
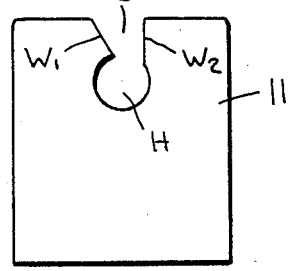
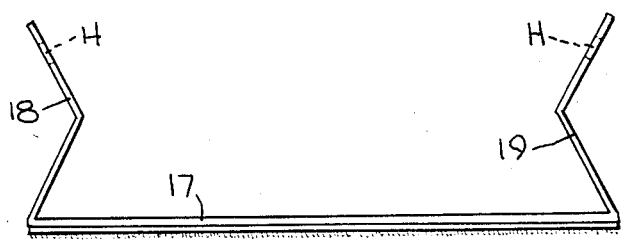
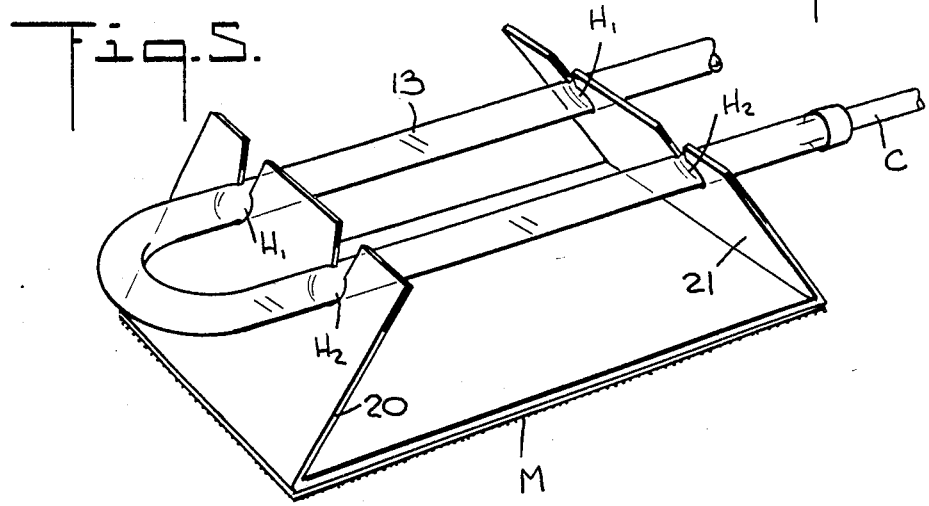

MEDICAL TUBING HOLDER

BACKGROUND OF INVENTION

1. Field of Invention

This invention relates generally to holders for immobilizing a flexible tubing at a site adjacent its point of connection to a medical device inserted in a patient to feed a therapeutic fluid into a vein or artery or to withdraw fluid from the patient, and more particularly to a detachable holder of this type which can be easily secured to the body of the patient at a desired site and readily detached therefrom.

2. State-of-the-Art

In an intravenous infusion (IV) system for plasma, glucose water or other therapeutic agents, a cannula or catheter is injected into a vein or artery of the patient and is coupled by an extended flexible plastic tubing to the fluid source. In extracting fluid from a patient, a similar tubing is extended between a medical device inserted in the patient through a nostril or other body cavity and a fluid receiver.

In all such situations, it is vital that the tubing adjacent to its point of coupling to the catheter or other medical device be immobilized in some way. In the absence of an immobilizer, a substantial tug on the tubing, which may occur inadvertently or when the patient changes his position, will displace or dislodge the catheter and may cause the catheter to cut the vein wall or to pull out of the vein, thereby causing the infusion to infiltrate the region surrounding the vein and resulting in a loss of intravenous therapy. This mishap necessitates restarting infusion therapy which is both inconvenient and possibly painful to the patient.

In order to effect immobilization of the tubing, the usual hospital practice is to improvise an immobilizer by means of strips of conventional adhesive tape. These strips are placed over the tubing and adhered to the skin of the patient at a position adjacent the point of infusion or insertion.

The security of a jury rig immobilizer of this type depends on the care exercised by the nurse or doctor who applies the tape; and should the tapes be hastily or carelessly applied, the immobilizer may be ineffective for its intended purpose.

It is important to bear in mind that the ability of the immobilizer to stabilize the tubing does not depend on the ability of the tape to adhere to the skin of the patient. Modern pressure-sensitive tapes of good quality, when applied to a skin surface, afford strong adherence thereto, particularly since the entire underface of the tape engages a corresponding skin surface. But when adhesive tape is applied over a flexible tubing having a small diameter, the region of adhesive contact between the tubing and the tape is quite limited, and the bond therebetween is not difficult to disrupt.

It is for this reason that various holders have heretofore been proposed to retain an infusion tube securely in place. Thus U.S. Pat. No. 3,834,380 to Boyd discloses a holder for IV tubing in the form of a longitudinally-split tubular clamp adapted to receive a section of the IV tubing. The clamp, which is formed of plastic, has an adhesive backing, making it possible to anchor the clamp on the skin of a patient. Various other devices for holding a catheter or an infusion tube in place are disclosed in U.S. Pat. Nos. 3,324,858; 3,630,195; 3,782,378 and 4,129,128.

In holders of the prior art type, the holder is directly adhered to a body site, and once so adhered, its orientation cannot be altered as may be necessary to properly position the holder relative to the point of body entry. Another drawback of such holders is that because they clamp onto the flexible tubing, they may occlude the fluid passage.

SUMMARY OF INVENTION

In view of the foregoing, the main object of this invention is to provide an improved holder for securely immobilizing a flexible tubing adjacent its point of connection to a catheter or other medical device inserted in a patient.

A significant advantage of a holder in accordance with the invention is that it can be applied to any site in the human body regardless of its contours. Also, the use of the holder is not limited to IV tubing, for it may be used with gastric and other forms of medical tubing.

More particularly, an object of the invention is to provide a holder of the above type which is low cost and therefore disposable, and which is light-weight, simple to use and comfortable.

Also an object of the invention is to provide a rigid cuff usable with the flexible tubing to prevent occlusion thereof when the tubing is retained by the holder.

Briefly stated, these objects are attained in a detachable holder for immobilizing a flexible tubing at a site adjacent its point of connection to a medical device inserted in a patient to feed a therapeutic fluid into a vein or artery or to withdraw fluid from the patient. The holder is formed by a flexible plastic strip having upstanding end wings provided with snap-in key hole slots in axial alignment. These slots are adapted to receive a short section of the tubing which then bridges the wings and is held thereby. Attached to the underside of the strip is one component of a hook and loop fabric fastener whose other component is bonded to the outer face of an adhesive tape. By adhering the tape to the skin of the patient at a position adjacent the inserted medical device and then fastening the holder thereto, one is able to immobilize the tubing to prevent a tug thereon from displacing the inserted medical device.

OUTLINE OF DRAWINGS

For a better understanding of the invention as well as other objects and further features thereof, reference is made to the following detailed description to be read in conjunction with the accompanying drawings, wherein:

FIG. 1 shows, in perspective, a preferred embodiment of a detachable holder for medical tubing in accordance with the invention, the holder being anchored on a body site;

FIG. 2 is an end view of one of the wings of the holder;

FIG. 3 shows, in perspective, a rigid cuff on the flexible tubing to prevent occlusion thereof;

FIG. 4 is a side view of another embodiment of the holder; and

FIG. 5 is a perspective view of still another embodiment of a holder.

DESCRIPTION OF INVENTION

First Embodiment

Referring now to FIGS. 1 and 2, there is shown a holder according to the invention formed by a flexible strip 10 of transparent material whose ends are bent up to form a pair of upstanding wings 11 and 12. Usable for the strip are such transparent plastics as polyethylene, PVC, polypropylene and other plastic materials having the required strength and resilience.

As best seen in FIG. 2, the corners of wings 11 and 12 are rounded to avoid sharp points. Formed in each wing is a slotted keyhole H whose diameter is appropriate to the diameter of the medical tubing 13 for which the holder is intended. The slot S leading into hole H has an inclined wall $W_1$ on one side thereof and a vertical wall $W_2$ on the other side to define a flexible flap. When the tubing is pressed into the keyhole, the flap is flexed by the pressure to temporarily enlarge the slot, the flap resuming its original position after the tubing is in place to lock the tubing within the hole.

When a short section of tubing 13 is inserted in the holes of wings 11 and 12, this section then bridges the wings and is retained by the holder. In order to prevent possible occlusion of the tubing, a cuff 14 is provided, as shown in FIG. 3. This cuff is formed of relatively rigid, clear synthetic plastic, the internal diameter of the cuff matching the external diameter of the tube so that the cuff is snugly held. The length of the cuff somewhat exceeds the distance between the holes so that the wings engage the cuff which prevent squeezing of the tubing extending through the cuff.

Tubing 13 is transparent so that one can observe flow therethrough. The holder and the cuff are also transparent so as not to interfere with this observation which is necessary to be sure fluid flow is unimpeded.

Means are provided to detachably anchor the holder at a site adjacent the point at which the tubing is coupled to a catheter inserted in a vein or artery or to a medical device inserted in the patient. A detachable anchor is desirable, for the user may find that the position of the holder is not quite right and may then have to change somewhat its orientation or location.

To this end, a pressure-sensitive adhesive tape 15 is provided whose outer face has formed thereon the female component F of a fabric hook and loop fastener. In a fastener of this type, which is available commercially in tape or in other forms, as VELCRO fasteners, the female component is constituted by a dense pile of tiny, soft Nylon loops. The male component is formed by a uniform array of tiny, stiff Nylon hooks, so that when the two components are pressed together, the hooks become embedded in the loops and are held thereby until the components are peeled apart. These fasteners are snag and jam-proof.

Bonded to the underside of holder strip 10 is a short tape having a male component M whose area corresponds to that of the strip. Adhesive tape 15 which is adhered to the body of the patient and carries female component F is broader than the male component and is of a length that depends on the skin region to be covered. Hence if this tape is to encircle the wrist of the patient, its length must be sufficient for this purpose.

If, for example, a medical device from which the tubing is extended is to be inserted in a nostril of the patient, tape 15 is long enough to provide an anchor across the forehead of the patient. Once tape 15 is in place, one then may press the holder thereon to cause the male component M on the underside thereof to engage the female component F on the tape.

Because the female component area is greater than that of the male component, the user has a choice of positions on the anchoring tape, and he may change the orientation of the holder, should this be necessary, without having to shift the position of the anchoring tape.

Other Embodiments

In the embodiment of the holder shown in FIG. 4, the strip 17, whose underside has a male component M bonded thereto, is provided with wings 18 and 19 in a compressible "V" formation to provide a somewhat springy holder for the tubing retained in slotted holes in these wings.

To be sure that a tug on the flexible tubing 13 will not result in the displacement of the catheter C coupled thereto, the holder provided for this purpose, as shown in FIG. 5, includes upstanding wings 20 and 21, each wing having a pair of slotted holes $H_1$ and $H_2$, so that the tubing may be held therein in a loop formation. Hence, a sharp tug on the tubing leading from the holder to the fluid source, if it acts to axially displace the tubing section bridging holes $H_1$ in the wings which are in axial alignment, will only serve to shorten the loop L, for it will not act to displace the parallel tubing section bridging axially-aligned holes $H_2$.

In another embodiment of the invention, which is not illustrated, the holder may be of molded flexible foam plastic to define a base having upstanding ledges at either end, each having a slotted keyhole into which one can press the tubing to be held, the base having bonded thereto the male component of the fabric fastener.

Further Features

While rigid cuff 14 shown in FIG. 3 is described above as functioning to prevent occlusion of the relatively soft and flexible tubing section pressed into the slotted keyholes of the holder, it serves other important functions. The cuffed tubing section makes it much easier to snap this section into the keyholes of the holder, and it also acts to positively lock the section therein and to resist displacement. In practice, the cuff may have a longitudinal slot therein, making it possible to snap the cuff onto the tubing section.

It is further to be noted that by making the holder of thin, resilient polypropylene, polycarbonate or other suitable plastic material, when this holder is anchored onto a contoured body site, the base of the holder will then conform thereto so that its entire area is firmly anchored.

Because the wings of the holder are inclined relative to its base, when the wings are bridged by the cuffed tubing section, the resultant configuration is trapezoidal and therefore resists folding of the wings to afford a highly stable holding structure despite the thinness of the holder plastic. And by locating the slotted keyholes on opposed wings at different levels, one can thereby cause the bridging tubing section to slope downwardly at an angle substantially corresponding to the entry angle of the catheter coupled to the tubing and inserted into the patient's vein, thereby avoiding a bend in the tubing at the point of coupling.

While there have been shown and described preferred embodiments of a MEDICAL TUBING HOLDER in accordance with the invention, it will be appreciated that many changes and modifications may be made therein without, however, departing from the essential spirit thereof.

We claim:

1. A detachable holder for immobilizing a flexible tubing at a site adjacent its point of connection to a catheter or other medical device used to feed fluid to a patient or to withdrawn fluid therefrom, said holder comprising:
- A. A strip of flexible synthetic plastic material forming a base having upstanding end wings each having a slotted keyhold therein, the keyholes being in axial alignment and having holes therein adapted to receive a short section of the tubing which then bridges the wings and is held thereby, each of said holes having a slot leading thereto defined by walls, at least one of which may be flexed to enlarge the slot to facilitate entry of the tubing, said base having holding means on the underside thereof, said wings being inclined to define with said short section a structurally stable trapezoid which resists folding of the wings; and
- B. detachable means cooperating with said holding means to detachably anchor said base on the skin surface of the patient at said site.

2. A holder as set forth in claim 1, wherein said holding means and said detachable means are constituted by a fabric hook and loop fastener, one of whose components is bonded to the underside of said base to form said holding means, the other component being formed on the outer face of an adhesive tape which is applied to said site to constitute the detachable means, said tape having a width and length greater than the width and length of the base whereby the user has a choice of positions on the tape and is able to change the orientation of the holder.

3. A holder as set forth in claim 1, wherein said hook component is bonded to said base and said loop component is formed on the tape.

4. A holder as set forth in claim 1, wherein said section of tubing is provided with a rigid cuff to prevent occlusion thereof and to facilitate insertion in the keyholes.

5. A holder as set forth in claim 1, wherein each wing has a pair of slotted keyholes whereby said tubing may be looped through the slots to define parallel short sections.

* * * * *